(12) United States Patent
Mangold et al.

(10) Patent No.: US 11,896,809 B2
(45) Date of Patent: Feb. 13, 2024

(54) RECEPTACLE FOR PHARMACEUTICAL PACKAGING WITH A THICKNESS PROFILE FOR A LUBRICANT LAYER

(71) Applicant: SCHOTT Pharma AG & Co. KGaA, Mainz (DE)

(72) Inventors: Stephanie Mangold, Schornsheim (DE); Raymond Moser, Engelburg (CH)

(73) Assignee: SCHOTT Pharma AG & Co. KGaA, Mainz (DE)

( * ) Notice: Subject to any disclaimer, the term of this patent is extended or adjusted under 35 U.S.C. 154(b) by 218 days.

(21) Appl. No.: 16/953,736

(22) Filed: Nov. 20, 2020

(65) Prior Publication Data

US 2021/0154413 A1    May 27, 2021

(30) Foreign Application Priority Data

Nov. 21, 2019  (EP) ..................................... 19210764
Mar. 6, 2020   (EP) ..................................... 20161542

(51) Int. Cl.
*A61M 5/315* (2006.01)
*A61M 5/31* (2006.01)
*A61M 5/00* (2006.01)

(52) U.S. Cl.
CPC ........ *A61M 5/31548* (2013.01); *A61M 5/002* (2013.01); *A61M 5/3129* (2013.01); *A61M 5/31591* (2013.01); *A61M 2005/3131* (2013.01); *A61M 2205/02* (2013.01)

(58) Field of Classification Search
CPC .............. A61M 5/31548; A61M 5/002; A61M 5/3129; A61M 5/31591; A61M 2005/3131; A61M 2205/02
See application file for complete search history.

(56) References Cited

U.S. PATENT DOCUMENTS

| 4,767,414 | A | 8/1988 | Williams et al. |
| 2007/0299402 | A1* | 12/2007 | Ishii ...................... A61L 27/303 |
| | | | 525/477 |
| 2010/0305513 | A1 | 12/2010 | Araki et al. |
| 2017/0182252 | A1* | 6/2017 | Hamel .................. B65B 7/2821 |

FOREIGN PATENT DOCUMENTS

EP         0 920 879 B1    4/2003

OTHER PUBLICATIONS

European Search Report dated Feb. 13, 2020 for European Patent Application No. 19210764 (5 pages).
Communication pursuant to Article 94(3) EPC for European Patent Application No. 19210764 (4 pages).

* cited by examiner

*Primary Examiner* — Lauren P Farrar
(74) *Attorney, Agent, or Firm* — Taylor IP, P.C.

(57) ABSTRACT

A receptacle includes: an elongate barrel section with an axial position p determined along an axis, the elongate barrel section extending from an axial position pA to an axial position pB; a side wall extending over the elongate barrel section and having an inner surface bordering an interior with a diameter; and a layer of a lubricant located on at least a part of the inner surface, a portion of the axis extends from a first axial position p1 to a second axial position p2; a mean thickness of the layer is determined in the portion; a position pm is the midpoint between p1 and p2; TA is a mean thickness of the layer for a section from p1 to pm; TB is a mean thickness of the layer for a section from pm to p2; a ratio TA:TB is in a range from 5:1 to 1:5.

19 Claims, 7 Drawing Sheets

US 11,896,809 B2

RECEPTACLE FOR PHARMACEUTICAL PACKAGING WITH A THICKNESS PROFILE FOR A LUBRICANT LAYER

CROSS REFERENCE TO RELATED APPLICATIONS

This application claims priority to European Patent Application EP 19210764.7 filed on Nov. 21, 2019, and European Patent Application No. 20161542.4 filed on Mar. 6, 2020, which are both incorporated in their entirety herein by reference.

BACKGROUND OF THE INVENTION

1. Field of the Invention

The present invention generally relates to a receptacle for pharmaceutical packaging characterized by a thickness profile for a lubricant layer. In particular, the present invention relates to a receptacle; a kit including a receptacle and a charge; an assembly including a receptacle, a charge and a liquid pharmaceutical composition; a process for the preparation of a receptacle and a use of a lubricant layer characterized by its thickness profile.

2. Description of the Related Art

Pharmaceutical material can be provided in a number of forms and contained in a variety of different containers. In the case of a liquid pharmaceutical material, some common examples are ampules, vials, cartridges and syringes. One widely used format employs a sliding plunger within a container for ejecting a liquid out of an aperture. One approach is to provide a lubricating layer on the inside of the container to facilitate sliding movement of the plunger.

U.S. Pat. No. 4,767,414 A describes plasma activation of an inner surface prior to application of a layer of silicone lubricant.

European Patent No. EP 0920879 B1 describes a recipe for a silicone-based mixture comprising reactive components and unreactive components.

There persists a need for improved approaches to lubrication of pharmaceutical containers, in particular for single-dose delivery.

SUMMARY OF THE INVENTION

Exemplary embodiments provided according to the present invention provide an improved receptacle for pharmaceutical packaging, in particular for single-dose delivery.

Exemplary embodiments provided according to the present invention provide an improved kit including a receptacle and a charge, in particular for single-dose delivery.

Exemplary embodiments provided according to the present invention provide an improved process for preparing a receptacle for pharmaceutical packaging, in particular for single-dose delivery.

Exemplary embodiments provided according to the present invention provide an improved assembly including a receptacle, a charge and a liquid pharmaceutical composition, in particular for single-dose delivery.

Exemplary embodiments provided according to the present invention provide a receptacle for pharmaceutical packaging having improved dynamic friction properties, in particular for single-dose delivery.

Exemplary embodiments provided according to the present invention provide a kit having improved dynamic friction properties, in particular for single-dose delivery.

Exemplary embodiments provided according to the present invention provide a process for preparing a receptacle for pharmaceutical packaging providing improved dynamic friction properties, in particular for single-dose delivery.

Exemplary embodiments provided according to the present invention provide an assembly having improved dynamic friction properties, in particular for single-dose delivery.

In some exemplary embodiments provided according to the present invention, a receptacle for pharmaceutical packaging includes: an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from a first axial position p1 to a second axial position p2 such that the following criteria are satisfied: both the first axial position p1 and the second axial position p2 lie between pA and pB; a portion length LX is a distance between the first axial position p1 and the second axial position p2; the portion length LX is at least a quarter of the elongate barrel section length LB; and the layer extends over the entire portion X. A mean thickness Tmean of the layer is determined in the portion X. A position pm is the midpoint between p1 and p2. TA is a mean thickness of the layer for a section from p1 to pm, TB is a mean thickness of the layer for a section from pm to p2, and a ratio TA:TB is in a range from 5:1 to 1:5. One or more of the following criteria are satisfied: the elongate barrel section length LB is in a range from 3 cm to 20 cm; a mean value of the diameter of the interior determined over the range pA to pB is in a range from 0.4 cm to 4 cm; a mean thickness of the sidewall determined over the range pA to pB is in a range from 0.3 mm to 4 mm; and a volume of the interior is in a range from 0.1 mL to 150 mL.

In some exemplary embodiments provided according to the present invention, a kit includes a receptacle and a charge. The receptacle includes: an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from a first axial position p1 to a second axial position p2 such that the following criteria are satisfied: both the first axial position p1 and the second axial position p2 lie between pA and pB; a portion length LX is a distance between the first axial position p1 and the second axial position p2; the portion length LX is at least a quarter of the elongate barrel section length LB; and the layer extends over the entire portion X. A mean thickness Tmean of the layer is determined in the portion X. A position pm is the midpoint between p1 and p2. TA is a mean thickness of the layer for a section from p1 to pm, TB is a mean thickness of the layer for a section from pm to p2, and a ratio TA:TB is in a range from 5:1 to 1:5. One or more of the following criteria are satisfied: the elongate barrel section length LB is in a range from 3 cm to 20 cm; a mean value of the diameter of the interior determined over the range pA to pB is in a range from 0.4 cm to 4 cm; a mean thickness of the sidewall determined over the range pA to pB is in a range from 0.3 mm to 4 mm; and a volume of the interior is in a range from 0.1 mL to 150 mL. The charge is adapted and arranged to be positioned in the interior such that: the charge seals a cross section of the interior between inner surfaces of the side walls; the charge has a front end at the axial position closest to pB at which the charge contacts the layer or the inner surface; the charge has a back end at the axial position closest to pA at which the charge contacts the layer or the inner surface; a length of the charge LC is a distance between the front end and the back end; the charge has a charge axial position that is an axial position of the front end; and the charge is movable in a direction parallel to the axis with a dynamic friction g that is a function of the charge axial position.

In some exemplary embodiments provided according to the present invention, an assembly includes a receptacle and a charge. The receptacle includes: an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB; a side wall extending over the elongate barrel section, the side wall having an inner surface bordering an interior, the interior having a diameter; and a layer of a lubricant located on at least a part of the inner surface. At a given axial position p on the axis between pA and pB, a thickness of the side wall, a thickness of the layer, and the diameter of the interior are each determined as an angular mean in a cross-sectional plane perpendicular to the axis at the axial position p. A portion X of the axis extends from a first axial position p1 to a second axial position p2 such that the following criteria are satisfied: both the first axial position p1 and the second axial position p2 lie between pA and pB; a portion length LX is a distance between the first axial position p1 and the second axial position p2; the portion length LX is at least a quarter of the elongate barrel section length LB; and the layer extends over the entire portion X. A mean thickness Tmean of the layer is determined in the portion X. A position pm is the midpoint between p1 and p2. TA is a mean thickness of the layer for a section from p1 to pm, TB is a mean thickness of the layer for a section from pm to p2, and a ratio TA:TB is in a range from 5:1 to 1:5. One or more of the following criteria are satisfied: the elongate barrel section length LB is in a range from 3 cm to 20 cm; a mean value of the diameter of the interior determined over the range pA to pB is in a range from 0.4 cm to 4 cm; a mean thickness of the sidewall determined over the range pA to pB is in a range from 0.3 mm to 4 mm; and a volume of the interior is in a range from 0.1 mL to 150 mL. The charge is positioned in the interior and seals a cross section of the interior. A liquid pharmaceutical composition is contained in the interior and located between the sealed cross section and the aperture. The assembly is adapted and arranged for the liquid pharmaceutical composition to be ejected through the aperture by movement of the charge in a direction parallel to the axis.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
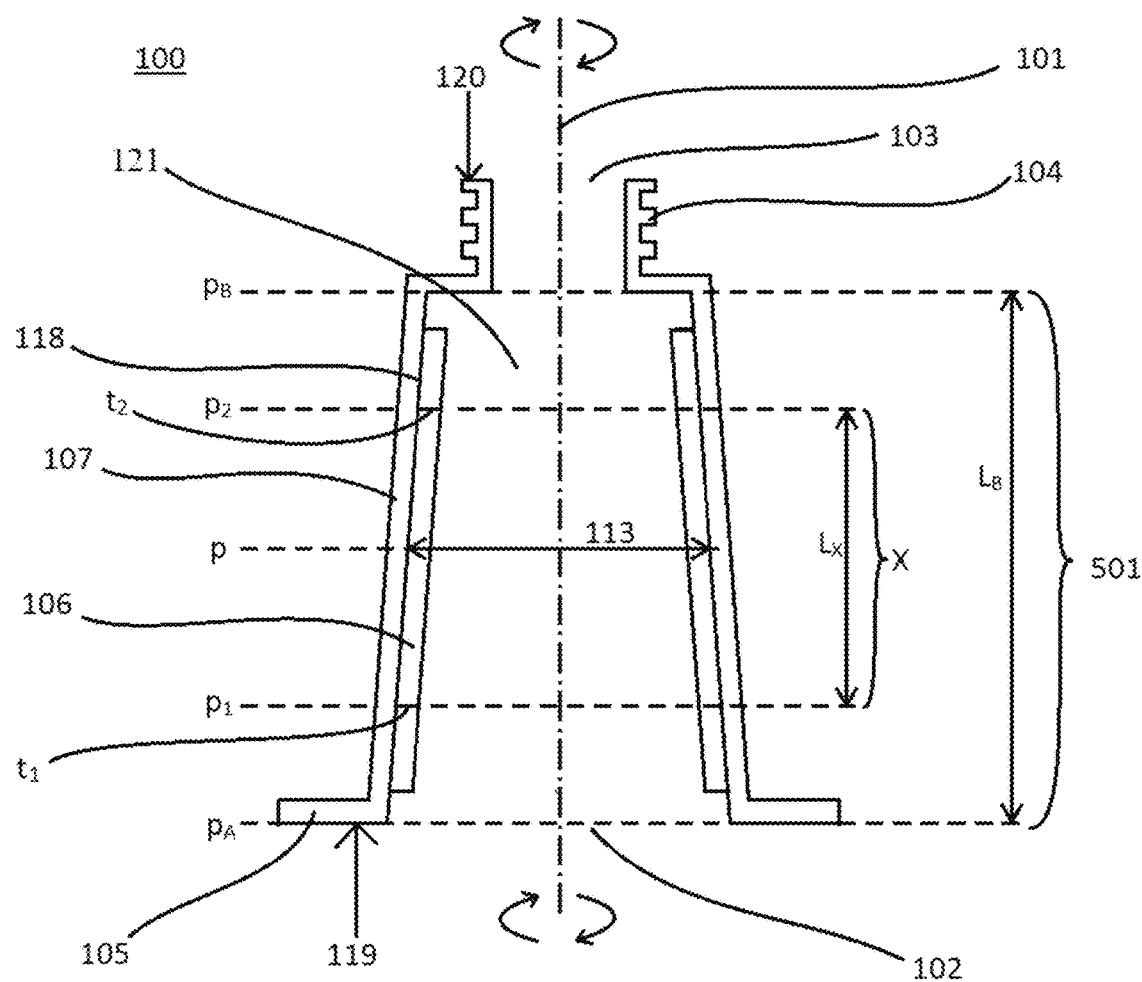
FIG. 1 illustrates a cross-sectional view of a receptacle with a layer of lubricant on an inner surface of a side wall.

In some exemplary embodiments provided according to the present invention, a receptacle for pharmaceutical packaging has an elongate barrel section. The elongate barrel section has a direction of elongate extension and an axis in the direction of elongate extension. An axial position p is determined along the axis. The elongate barrel section extends from an axial position pA to an axial position pB. An elongate barrel section length LB is the distance between pA and pB. The receptacle has a side wall extending over the elongate barrel section, the side wall having an inner surface bordering an interior, the interior having a diameter. A layer of a lubricant is located on at least a part of the inner surface. At a given axial position p on the axis between pA and pB, the thickness of the side wall, the thickness of the layer, and the diameter of the interior are each determined as an angular mean in a cross-sectional plane perpendicular to the axis at the axial position p. A portion X of the axis extends from an axial position p1 to an axial position p2 such that the following criteria are satisfied: both p1 and p2 lie between pA and pB; a portion length LX is the distance between p1 and p2; LX is at least a quarter of LB, such as at least a half of LB, at least 80% of LB, or at least 90% of LB; and the layer extends over the entire portion X. Tmean is a mean thickness of the layer determined in the portion X. A position pm is the midpoint between p1 and p2. TA is a mean thickness of the layer for a section from p1 to pm. TB is a mean thickness of the layer for a section from pm to p2. The ratio TA:TB is in the range from 5:1 to 1:5, such as in the range from 3:1 to 1:3, in the range from 2:1 to 1:2, or in the range from 4:3 to 3:4. One or more of the following receptacle criteria are satisfied:
   i. the length LB is in the range from 3 to 20 cm, such as in the range from 4 to 15 cm, in the range from 5 to 12 cm, or in the range from 6 to 8 cm;
   ii. the mean value of the diameter of the interior determined over the range pA to pB is in the range from 0.4 to 4 cm, such as in the range from 0.6 to 3 cm, in the range from 0.8 to 2.5 cm, or in the range from 1 to 2 cm;
   iii. the mean thickness of the sidewall determined over the range pA to pB is in the range from 0.3 to 4 mm, such as in the range from 0.7 to 3 mm, in the range from 1.1 to 2 mm, or in the range from 1.4 to 1.8 mm; and
   iv. the volume of the interior is in the range from 0.1 to 150 ml, such as in the range from 0.5 to 50 ml, in the range from 1 to 25 ml, in the range from 2 to 10 ml, or in the range from 3 to 5 ml.

In some embodiments, Tmean is in the range from 50 nm to 4100 nm.

In some embodiments, the following combinations of the receptacle criteria i. to iv. are fulfilled: i., ii., iii., iv., i.+ii., i.+iii., i.+iv., ii.+iii., ii.+iv., iii.+iv., i.+ii.+iii., i.+ii.+iv., i.+iii.+iv., ii.+iii.+iv & i.+ii.+iii.+iv.

In some embodiments, the mean thickness Tmean of the layer is in the range from 100 nm to 3000 nm, such as in the range from 300 to 2000 nm, in the range from 500 nm to 1500 nm, or in the range from 700 nm to 1200 nm.

In some embodiments, the inner surface of the side wall has a roughness rrms and the ratio rrms:Tmean is in the range from 1:2 to 1:20, such as in the range from 1:3 to 1:15 or in the range from 1:4 to 1:10.

In some embodiments, the layer has a maximum layer thickness Tmax determined between p1 and p2, a minimum layer thickness Tmin determined between p1 and p2 and the value of Tmin/Tmax is at least 0.7, such as at least, 0.75, 0.8, 0.9, or 0.95.

In some embodiments, the side wall comprises a plastic or a glass or both.

In some embodiments, the lubricant comprises one or more silicone oils. The lubricant may comprise in total at least 5 wt. %, at least 15 wt. %, or at least 25 wt. % of one or more silicone oils, based on the total weight of the lubricant of the layer.

In some embodiments, the one or more silicone oils are at least partially contained in a matrix bound to the inner surface.

In some embodiments, the matrix is a polymer, such as a crosslinked polymer.

In some embodiments, the polymer comprises SiO-containing repeating units. An exemplary polymer is a polysiloxane, such as a crosslinked polysiloxane.

In some embodiments, the interior is cylindrical or truncated conical over the elongate barrel section. An exemplary truncated cone has a cone aperture in the range from 0.04° to 0.4°, such as in the range from 0.08° to 0.25° or in the range from 0.1° to 0.2°.

In some embodiments, the receptacle includes a first aperture at a first end and a second aperture at a second end. The first aperture may have a greater area than the second aperture, such as at least 50% greater, at least 100% greater, or at least 200% greater, based on the surface area of the second aperture. In some alternative embodiments, the receptacle has a first aperture at a first end and a dead end at a second end.

In some embodiments, the internal diameter at p1 is d1 and the internal diameter at p2 is d2 and d1 is greater than d2. d1 may be at least 0.05% greater than d2, such as at least 0.1% or at least 0.2%, based on the diameter d2. d1 may be up to 5% greater than d2, such as up to 4% or up to 3%, based on the diameter d2.

In some embodiments, the receptacle includes an attachment element at an aperture. An attachment element may be at an end, such as at a second end. An exemplary attachment element is adapted and arranged for attaching one or both selected from the group consisting of a needle and a tube. Some exemplary attachment elements are a screw thread, a latch, a Luer fitting and a bayonet-style fitting.

In some embodiments, the layer has a minimum thickness tmin determined in the portion X of at least 60 nm, such as at least 90 nm, at least 100 nm, or at least 110 nm.

In some exemplary embodiments provided according to the present invention, a kit includes as kit parts the previously described receptacle and a charge. The charge is adapted and arranged to be positioned in the interior such that: the charge seals a cross section of the interior between the inner surfaces of the side walls; the charge has a front end at the axial position closest to pB at which the charge contacts the layer or the inner surface; the charge has a back end at the axial position closest to pA at which the charge contacts the layer or the inner surface; a length of the charge LC is the distance between the front end and the back end; and the charge has a charge axial position, being the axial position of the front end.

The charge is movable in a direction parallel to the axis with a dynamic friction g, g being a function of the charge axial position.

In some embodiments, for charge axial positions in the range from p1+LC to p2, the dynamic friction g has a maximum value gmax, a minimum value gmin and a mean value gmean and the value of gmin/gmax is at least 0.7, such as at least 0.8, at least 0.90, at least 0.94, or at least 0.98.

In some embodiments, for charge axial positions in the range from p1+LC to p2, the dynamic friction g has a standard deviation gSD less than 2 N, such as less than 1 N, less than 0.5 N, or less than 0.2 N.

In some exemplary embodiments provided according to the present invention, an assembly includes the previously described receptacle and a charge. The receptacle has an aperture; the charge is positioned in the interior sealing a cross section of the interior; the interior contains a liquid pharmaceutical composition, located between the sealed cross section and the aperture; and the assembly is adapted and arranged for the liquid pharmaceutical composition to be ejected through the aperture by movement of the charge in a direction parallel to the axis.

In some exemplary embodiments provided according to the present invention, a process for preparing the previously described receptacle, kit, or assembly includes a process step of applying the layer of lubricant by spreading with a spreading tool.

In some exemplary embodiments provided according to the present invention, a use of a layer of lubricant for improving uniformity of dynamic friction in a pharmaceutical receptacle having a layer of a lubricant is provided. The ratio of the mean thickness over a first half of the layer to the mean thickness over a second half of the layer TA:TB is in the range from 1:5 to 5:1, such as in the range from 3:1 to 1:3, in the range from 2:1 to 1:2, or in the range from 4:3 to 3:4.

Diameters, Layer Thicknesses and Roughness

The axis of the receptacle is used to determine axial position. At a given axial position, the side wall is a perimeter having a thickness lying in a cross-sectional plane perpendicular to the axis, likewise for the lubricant layer. Internal diameter, thickness of the lubricant layer, thickness of the side wall and surface roughness at a given point along the axis may be mean values determined around a perimeter. A mean around a perimeter is an angular mean. An angular mean may be determined by measuring at 8 points around the perimeter, the 8 points being separated by equal angles.

Receptacle

An exemplary receptacle is adapted and arranged to contain a pharmaceutical liquid. Some exemplary receptacles are syringes, syringe barrels, cartridges, dead-end containers and vials.

An exemplary receptacle has one or more apertures. An aperture may be located at an end of the receptacle. In some embodiments, the receptacle has one aperture. In some embodiments, the receptacle has two apertures.

The receptacle may have two ends, a first end and a second end.

An exemplary receptacle has a first aperture at a first end. One type of exemplary receptacle has a second aperture at a second end. Another type of exemplary receptacle has a dead end at a second end.

Elongate Barrel Section

The receptacle has an elongate barrel section. The elongate barrel section denominates a section of the receptacle. The receptacle may have further sections outside of the elongate barrel section. Another term for an elongate barrel section is a tube section. An exemplary elongate barrel section is tubular.

Possible embodiments of the elongate barrel section and the axis are described herein in mathematical terms, for example as axes of symmetry, rotation or revolution, surfaces and solids of revolution and shapes such as cylinders and truncated cones. These embodiments are to be understood as allowing some variation from these precise mathematical concepts. Suitable variations from the mathematic concepts are those which do not inhibit the receptacle from functioning as a plunger system in cooperation with a charge.

The elongate barrel section has an axis. The axis may be an axis of rotation for the elongate barrel section. The axis may be an axis of revolution for the elongate barrel section. The side wall may be a solid of revolution about the axis. The inner surface may be a surface of revolution about the axis. The layer may be a solid of revolution about the axis.

The axis defines an axial position p. The axial position p is an axial position along the axis. Herein, the symbol p denotes an axial position in general terms and specific axial positions are denoted by the letter p with a subscript.

An axial position p along the axis is used as a parameter to describe the locations of points or cross-sections along the elongate barrel section, for example on the side wall. The axial position of a point not on the axis is found by projecting the point onto the axis by a displacement vector perpendicular to the axis. A cross section is a plane perpendicular to the axis. The axial position of a cross section is found at the point where the cross section meets the axis.

The elongate barrel section extends from an axial position pA to an axial position pB. The elongate barrel section is contained by a cross section at pA and a cross section at pB.

The receptacle has a side wall extending over the elongate barrel section. The side wall has an inner surface. The inner surface borders an interior. Exemplary shapes for the side wall are a hollow cylinder, a hollow prism and a hollow truncated cone. An exemplary hollow truncated cone has a diameter which decreases from pA to pB. Exemplary shapes for the interior are a cylinder, a prism and a truncated cone. An exemplary truncated cone has a diameter which decreases from pA to pB.

The inner surface may be smooth or may have some roughness.

The thickness of the side wall may be measured as a difference in radial distance from the axis of the inner surface and an outer surface of the side wall.

The thickness of the layer may be measured as a difference in radial distance from the axis of an inner surface of the layer and the inner surface of the side wall.

Exemplary materials for the side wall are polymers and glasses.

In some embodiments, the side wall comprises a polymer, and in some embodiments is made out of a polymer. The polymer may be one or both selected from the group consisting of: one or more cyclic olefin copolymers and one or more cyclic olefin polymers. In some embodiments, the polymer is at least 30 wt. % of the side wall, such as at least 50 wt. %, at least 80 wt. %, or about 100 wt. %.

In some embodiments, the side wall comprises a glass, and in some embodiments is made of a glass. An exemplary glass in this context comprises one or more selected from the group consisting of: silicon, boron and aluminum. One exemplary glass comprises boron and silicon. One exemplary glass is a borosilicate glass. One exemplary glass comprises aluminum and silicon. One exemplary glass is an aluminosilicate glass. In some embodiments, the glass is at least 30 wt. % of the side wall, such as at least 50 wt. %, at least 80 wt. %, or about 100 wt. %.

Lubricant Layer

The layer of lubricant is located on the inner surface of the side wall. The lubricant layer may extend over the entire elongate barrel section or just a part of it. The lubricant layer extends over the entire portion X.

An exemplary lubricant is a silicone-based lubricant.

An exemplary lubricant comprises one or more polysiloxanes.

An exemplary lubricant comprises one or more silicone oils, with a total content of silicone oils in the range from 10 to 50 wt. %, such as in the range from 20 to 40 wt. % or in the range from 25 to 35 wt. %, based on the total weight of the lubricant. An exemplary silicone oil is a poly dimethyl silicone.

An exemplary lubricant comprises a crosslinked poly siloxane matrix, with a total content of crosslinked poly siloxane matrix in the range from 50 to 90 wt. %, such as in the range from 60 to 80 wt. % or in the range from 65 to 75 wt. %, based on the total weight of the lubricant.

An exemplary lubricant may be prepared from a mixture comprising one or more, such as all, of the following:
a reactive polysiloxane
an unreactive polysiloxane
a catalyst
a diluent An exemplary reactive polysiloxane is adapted and arranged to undergo a cross-linking reaction to obtain a cross-linked network. The cross-linking may be catalyzed by the catalyst.

An exemplary unreactive polysiloxane does not undergo a cross-linking reaction. An exemplary unreactive polysiloxane comprises one or more alkyl groups. A further exemplary unreactive polysiloxane is fully substituted with alkyl groups.

An exemplary catalyst catalyses a reaction to cross-link polysiloxanes.

An exemplary diluent solves one or more of the other constituents of the mixture. An exemplary diluent is silicon based. An exemplary diluent is a short chain polysiloxane having 6 repeat units or less. An exemplary diluent is hexamethyl disiloxane.

An exemplary lubricant contains not more than 10 wt. % water, based on the total weight of the lubricant, such as not more than 5 wt. % or not more than 1 wt. %.

The lubricant layer has a thickness profile from p1 to p2.

The thickness t2 of the layer at p2 may be similar to the thickness t1 at p1. In some embodiments, the ratio t2:t1 is in the range from 5:1 to 1:5, such as in the range from 3:1 to 1:3, in the range from 2:1 to 1:2, or in the range from 4:3 to 3:4.

The thickness may have a reduced variance. In some embodiments, the layer has a maximum layer thickness Tmax determined between p1 and p2, a minimum layer thickness Tmin determined between p1 and p2 and the ratio Tmin/Tmax is at least 0.7, such as at least 0.8, at least 0.9, at least 0.95, or at least 0.98.

In some embodiments, the layer extends over at least 70%, such as at least 80%, at least 90%, or about 100% of the length LB of the elongate barrel section. In some embodiments, the lubricant extends over 20 to 60% of the length LB elongate barrel section.

In some embodiments, the lubricant layer has a minimum thickness tmin determined between p1 and p2 inclusive of at least 60 nm, such as at least 90 nm, at least 100 nm, or at least 110 nm.

In some embodiments, the layer has a minimum thickness tmin determined between p1 and p2 inclusive which is greater than the mean roughness of the inner surface of the side wall between p1 and p2, such as at least 20 nm greater, at least 40 nm, or at least 60 nm greater.

In some embodiments, the layer of lubricant can be cured after application. Exemplary ways of curing are thermal or radiation induced or a combination of both. Some exemplary ways of curing are application of UV radiation and application of IR radiation.

Liquid Pharmaceutical Composition

The receptacle is for pharmaceutical packaging. An exemplary receptacle is adapted and arranged to contain a liquid.

A liquid pharmaceutical composition may comprise an active compound.

A liquid pharmaceutical composition is a fluid.

An exemplary amount of liquid pharmaceutical composition is in the range from 0.1 to 100 ml, such as in the range from 0.5 to 70 ml, in the range from 0.8 to 40 ml, in the range from 1 to 10 ml, or in the range from 2 to 5 ml.

Charge

The receptacle is adapted and arranged to accommodate a charge. An exemplary charge is adapted and arranged to be accommodated in the receptacle. The receptacle and charge may be complementary such that the charge can be introduced into the interior of the receptacle and such that the charge can move within the interior in a direction parallel to the axis.

An exemplary charge is made of an elastic material or comprises a part made of an elastic material. The charge may be adapted and arranged to seal a cross-section of the interior. The charge may be adapted and arranged to move inside the receptacle, such as along the axis defined by the elongate extension of the receptacle. When inside the receptacle, movement of the charge may be resisted by a frictional force between the charge and an inside surface of the receptacle.

The charge may be attached to an elongate rod adapted and arranged to push or pull the charge in a direction parallel to the axis.

An exemplary charge is a plunger.

Charge Axial Position

When in position in the receptacle, the charge makes contact with the layer or the inner surface or both. The front end of the charge is the point of forwardmost contact, in a direction from pA to pB, of the charge with the layer or the inner surface. The back end of the charge is the point of backmost contact, in a direction from pA to pB, of the charge with the layer or the inner surface. The charge axial position is the axial position of the front end.

The distance between the front end and the back end of the charge is the charge length LC.

Kit

In some exemplary embodiments provided according to the present invention, a kit includes a receptacle provided according to the present invention and a charge provided according to the present invention.

The charge and the receptacle may be complementary such that the charge can be accommodated in the receptacle and can move within the interior in a direction parallel to the axis.

Frictional Forces

The movement of the charge within the receptacle is accompanied by a frictional force between the charge and the inner surface of the side wall and or the layer. The frictional force comprises both a stiction which resists the setting in motion of the charge relative to the receptacle and a dynamic friction which acts whilst the charge is in movement.

The dynamic friction is dependent on the charge axial position. The dynamic friction at a given charge axial position p may be determined by starting the charge at charge axial position p1+LC and moving the charge from p1+LC to p2 at a constant speed of 100 mm/minute. The value of dynamic friction at charge axial position p is the force required to maintain the speed of the charge at 100 mm/minute when the charge is at charge axial position p. A method for determining the dynamic friction is presented in the drawings.

Assembly

In some exemplary embodiments provided according to the present invention, an assembly includes a receptacle, a charge and a liquid pharmaceutical composition. The charge is positioned inside the receptacle to seal a cross-section of the interior. The liquid pharmaceutical composition is present in the interior between the sealed cross-section and an aperture of the receptacle.

In some embodiments, the liquid pharmaceutical composition fills at least 50 vol. % of the interior, such as at least 70 vol. % or 80 vol. %.

In some embodiments, the liquid pharmaceutical composition fills less than 50 vol. % of the interior, such as less than 30 vol. % or less than 20 vol. %.

The assembly may be adapted and arranged such that the liquid pharmaceutical composition can be ejected from the interior by moving the charge in a direction parallel to the axis towards the second end.

An exemplary assembly functions as a plunger system in which the liquid pharmaceutical composition can be ejected from the receptacle through movement of the charge.

An exemplary receptacle has an attachment element, such as at an end. An exemplary attachment element is adapted and arranged for attaching a needle or tube. A needle or tube may be attached to the receptacle in the assembly.

Luer Fitting

Exemplary receptacles, be they receptacles as such or as part of a kit or an assembly, have a Luer fitting. An exemplary Luer fitting is compatible with ISO 80369. Exemplary Luer fittings are Luer lock fittings and slip tip fittings. In some embodiments, the receptacle has a Luer lock fitting. In some embodiments, the receptacle has a slip tip fitting. An exemplary Luer fitting is a male Luer fitting. Exemplary Luer lock fittings are one-piece Luer lock fittings and two-piece Luer lock fittings. In some embodiments, the receptacle has a one-piece Luer lock fitting. In some embodiments, the receptacle has a two-piece Luer lock fitting.

Process for Preparation

A receptacle provided according to the present invention may be prepared by providing a receptacle without a layer lubricant and applying a layer of lubricant to the inner surface of the side wall of the receptacle. Exemplary methods for applying the layer are spreading and wiping with a suitable tool.

An assembly may be prepared by the following steps:
providing a receptacle according to the present invention;
introducing a charge into the receptacle, such as via a first en via a first aperture;
introducing a liquid pharmaceutical composition into the interior of the receptacle, such as via a second end via a second aperture.

Referring now to the drawings, FIG. 1 shows a cross-sectional view of a receptacle 100 with a lubricant layer 106 on an inner surface 118 of a side wall 107. The receptacle 100 has a first end 119 and a second end 120. At the first end 119 is a first aperture 102 and an outwardly protruding flange 105. At the second end 120 is a second aperture 103 and an attachment element 104, in this case a screw thread, for attaching a needle fitting. The receptacle 100 has an elongate barrel section 501 extending from an axial position pA to an axial position pB. As illustrated in FIG. 1, pA is closer to the first end 119 than pB and pB is closer to the second end 120 than pA. In this case, the elongate barrel section 501 has a hollow truncated conical shape with a greater diameter at pA than at pB. The length of the elongate barrel section 501 is LB. The axis 101 is in the direction of elongate extension of the receptacle 100 and is the axis of rotation of the elongate barrel section 501. The side wall 107 has an inner surface 118, on which is present a layer 106 of lubricant. The layer 106 extends over some, but not all of the side wall 107, not reaching the ends pA and pB. A portion X of the elongate barrel section 501 runs between axial positions p1, which is closer to pA (and the first end 119) than pB (and the second end 120), to p2, which is closer to pB (and the second end 120) than pA (and the first end 119). The portion X is an abstract portion selected according to the criteria presented herein. The end points p1 and p2 both lie within the bounds of the layer 106. The purpose of selecting the abstract portion X of the elongate barrel section 501 is to ensure that irregularities at the ends of the elongate barrel section 501 are avoided, in particular since the layer 106 may not extend all the way to the ends pA and pB, as in this example. Axial positions along the receptacle 100 are measured along the axis 101. Axial positions may be given with reference to p1 as a fiduciary zero point. Shown is a general axial position p as well as the internal diameter 118 between of the inner surfaces 118 of the side walls 107 at that axial position. The thicknesses t1 at axial position p1 and t2 at axial position p2 are shown.

FIGS. 2A to 2G show a single-push movement of a charge 203 in a receptacle 100. The series of figures demonstrates how the charge 203 may be pushed in a single push along the axis 101 of the receptacle 100 at a constant speed of 100 mm/min. The process presented can also be used to construct a profile of the dynamic friction between the charge 203 and the side wall 107/lubricant layer 106 as a function of axial position along the axis 101. Because the movement is performed in a single push, a stiction force is only relevant for the start point. The process is performed using a TesT 106.2 kN device commercially available from TesT GmbH, Germany.

Figure 2A:
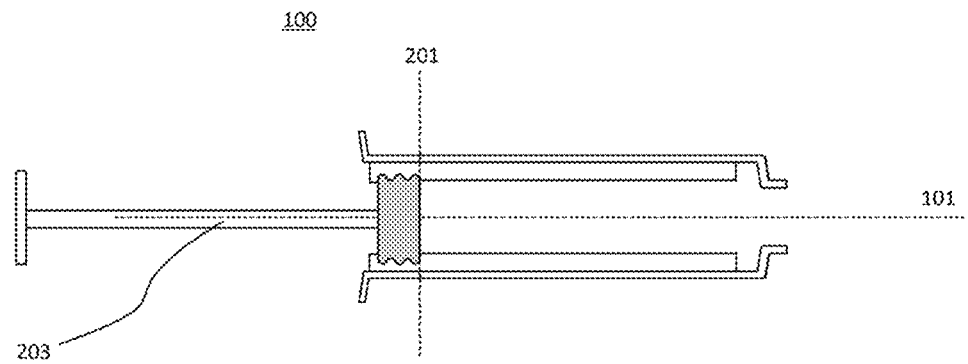
FIGS. 2A, 2B, 2C, 2D, 2E, 2F, and 2G illustrate a single-push movement of a charge in a receptacle.

FIG. 2A shows a receptacle 100 ready for single-push movement of a charge 203. The arrangement is the same as in FIG. 1.

FIG. 2A shows the receptacle 100 of FIG. 2A, in which a pushing force 207 is applied to the elongate rod 202 in a direction along the axis 101. The force 207 is transferred to the charge 203. In the figure, the force 207 is inferior to the stiction force at the initial axial position 201 and the charge 203 is at rest, with the pushing force 207 cancelled out by the static frictional force between the charge 203 and the side walls 207/lubricant layer 106. The stiction force at the axial position 201 is determined as the force 207 at which the charge 203 starts to move along the axis 101.

Figure 2B:
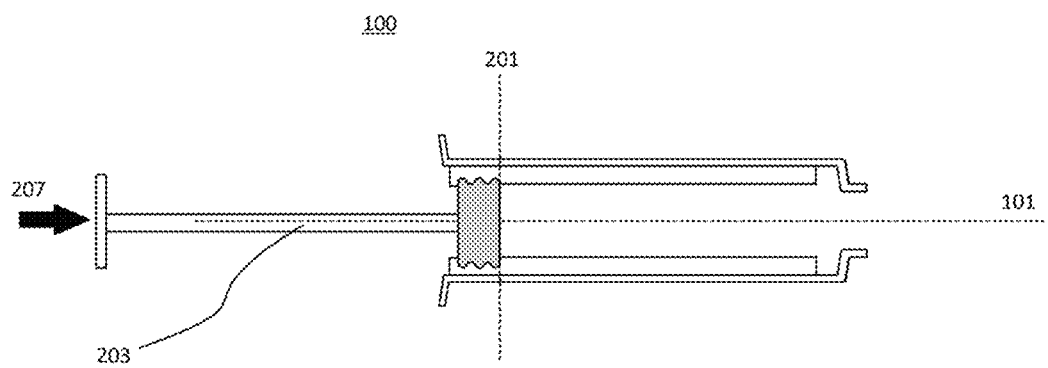
Figure 2C:
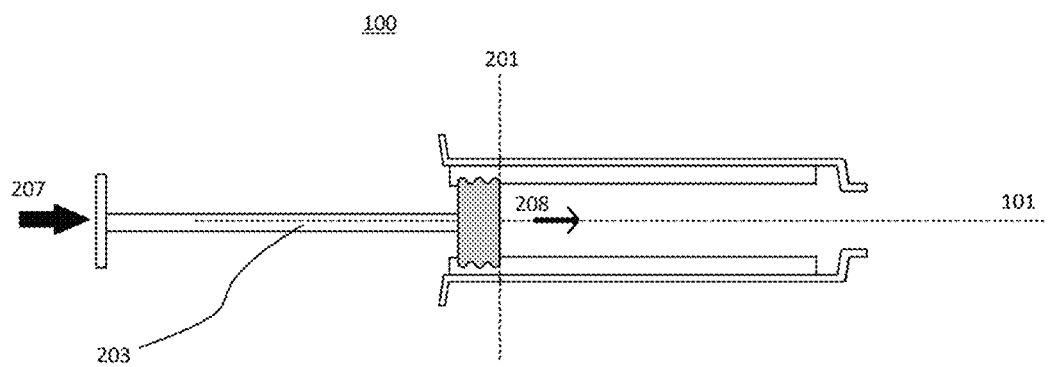

FIG. 2C shows the receptacle 100 immediately after the pushing force 207 in FIG. 2B exceeds the stiction force at axial position 201 to put the charge 203 into motion. The charge 203 is depicted at the axial position 201, but in motion 208 along the axis 101. The pushing force 207 is equal to the dynamic friction at axial position 201 and the charge 203 is in a state of constant velocity along the axis 101.

Figure 2D:
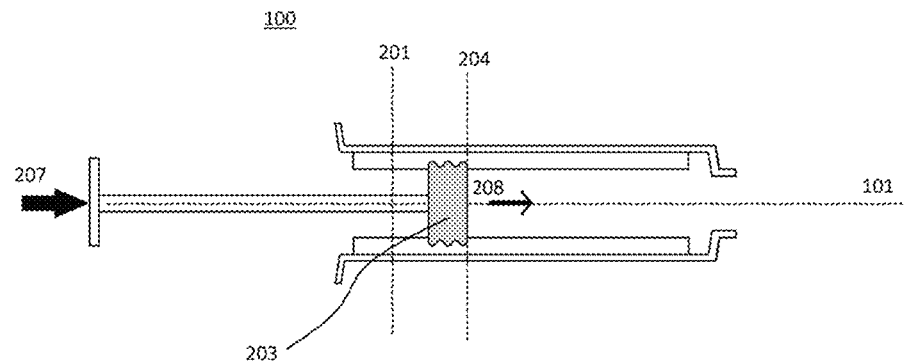

FIG. 2D shows the receptacle 100 subsequent to that of FIG. 2C, in which the charge 203 has travelled a distance from 201 to 204 along the axis 101. The charge 203 is still in motion 208 with constant velocity with the pushing force 207 being equal to the dynamic friction at axial position 204. Therefore, the pushing force is a measure of the dynamic friction at axial position 204.

Figure 2E:
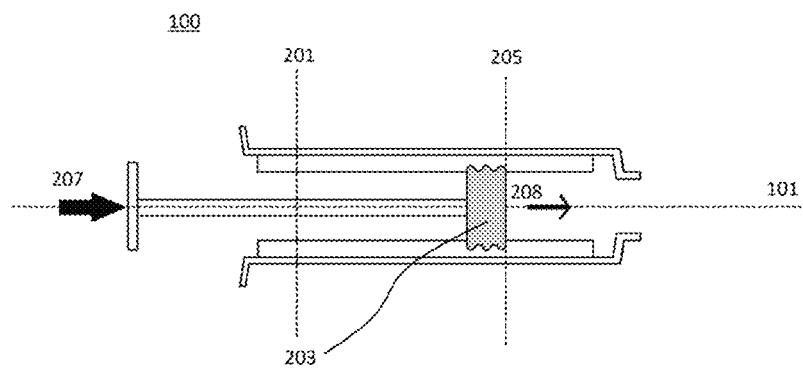

FIG. 2E shows the receptacle 100 after the situation of FIG. 2D. The charge 203 has travelled a further distance from 204 to 205 along the axis 101. The charge is still in motion with constant velocity with the pushing force 207 and the dynamic friction being equal. The pushing force 207 is thus a measure of the dynamic friction at axial position 205.

Figure 2F:
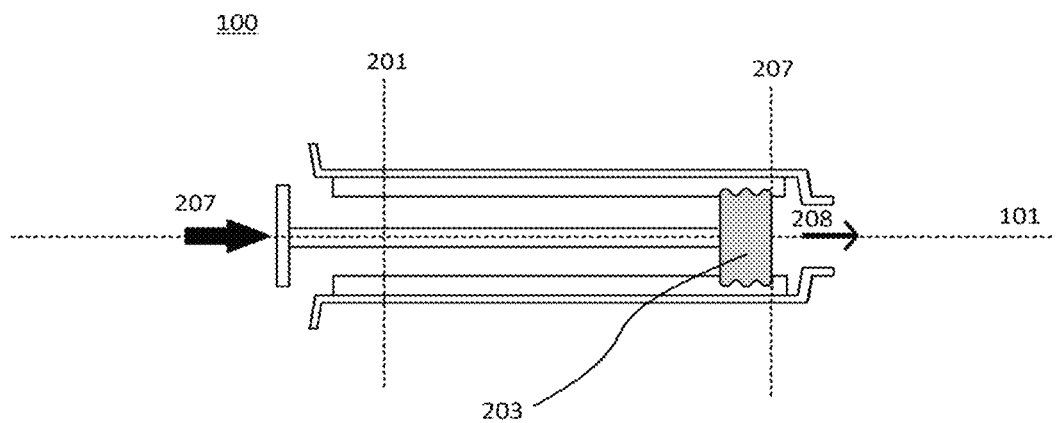

FIG. 2F shows the receptacle 100 after the situation of FIG. 2E. The charge 203 has travelled a further distance from 205 to 206 along the axis 101. The charge is still in motion with constant velocity with the pushing force 207 and the dynamic friction being equal. The pushing force 207 is thus a measure of the dynamic friction at axial position 206.

Figure 2G:
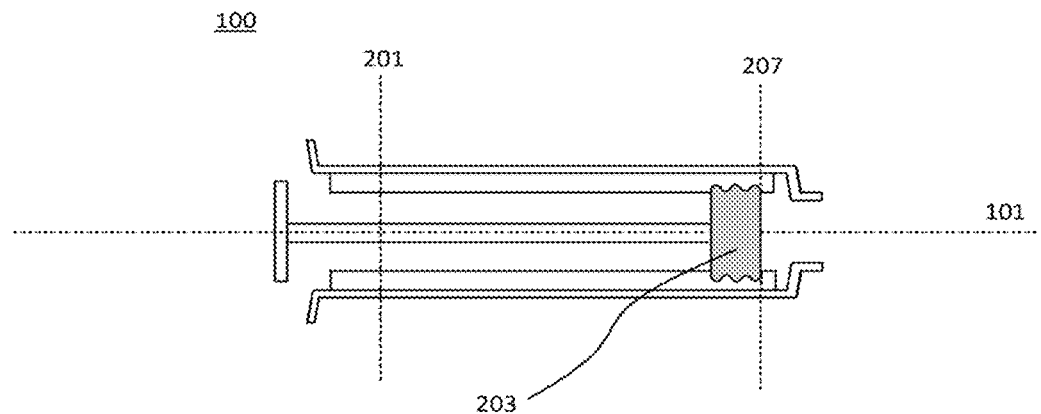

FIG. 2G shows the receptacle in which the pushing force has been released at axial position. The axial position 206, is where the front end of the charge has arrived at p2, close to the end of the lubricated layer and is in its final rest axial position.

The dynamic friction at any point along the axis 101 is provided directly as the pushing force required at that point to maintain constant velocity (100 mm/min) of the charge 203 along the axis 101. The dynamic friction at points 201, 204, 205 and 206 are measured at the stages of FIGS. 2C, 2D, 2E and 2F respectively.

Figure 3:
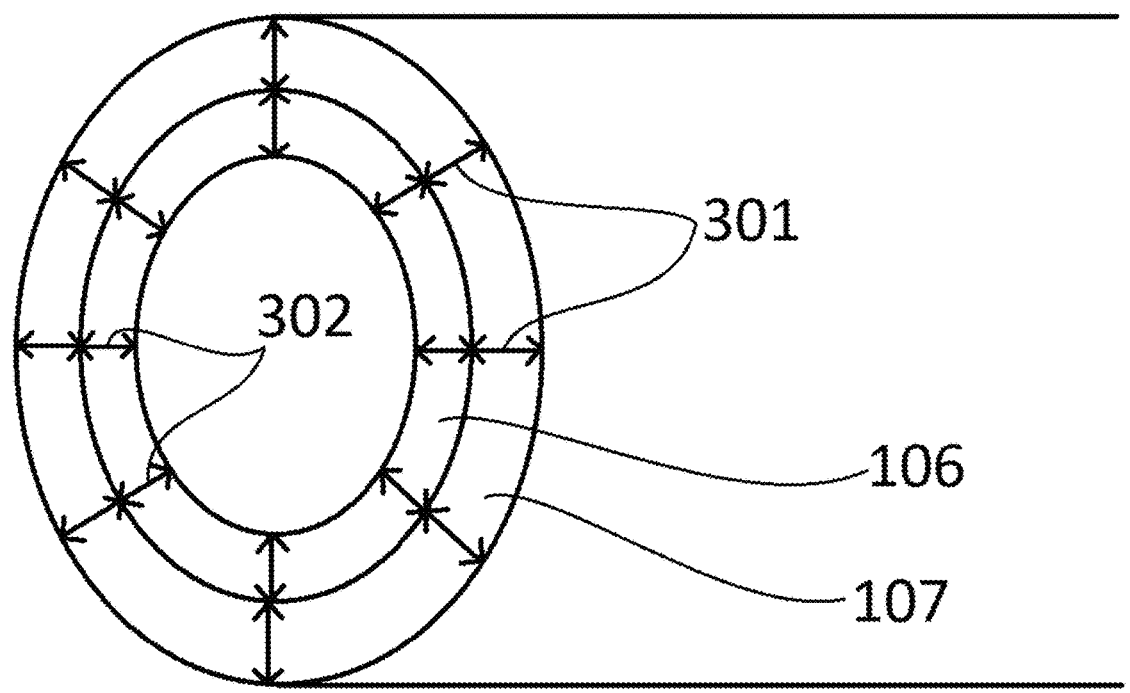
FIG. 3 illustrates a cross-sectional view through the receptacle.

FIG. 3 shows a cross-sectional view through the receptacle 100 at an axial position p along the axis 101. The side wall 107 and the lubricant layer 106 are shown as concentric circular bands. The thickness 301 of the side wall 107 and the thickness 302 of the lubricant layer 106 are each shown at 8 equidistant points around the circle. A thickness of a side wall 107 or a layer 106 of lubricant at an axial position p is a mean of the thickness around the circle. This is measured as the mean of a number of equally spaced sample points around the circle, in this case 8.

FIGS. 4A to 4E show the process of preparing an assembly and ejecting a pharmaceutical product 401.

Figure 4A:
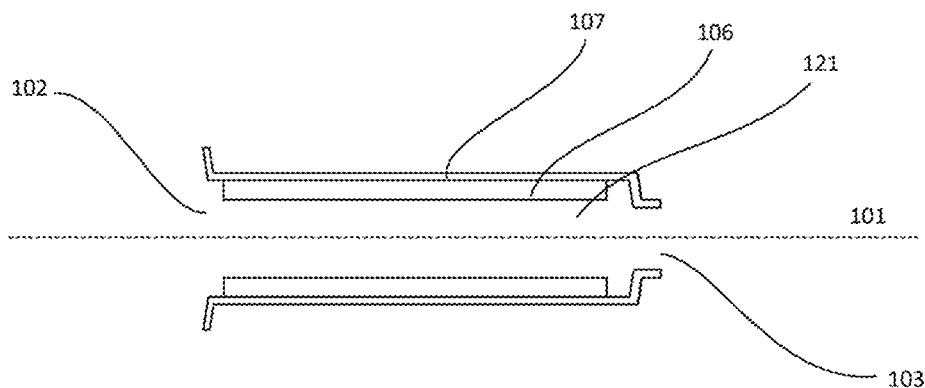
FIGS. 4A, 4B, 4C, 4D, and 4E illustrate the process of preparing an assembly and ejecting a pharmaceutical product.

FIG. 4A shows a receptacle 100, ready for forming an assembly. The receptacle 100 has an axis of rotation 101, a side wall 107 and an interior 121. A layer 106 of lubricant is present on the inside of the receptacle 100. The layer 106 of lubricant has been cured by heating at 175° C. for 20 seconds. The receptacle 100 has a first aperture 102 and a second aperture 103.

Figure 4B:
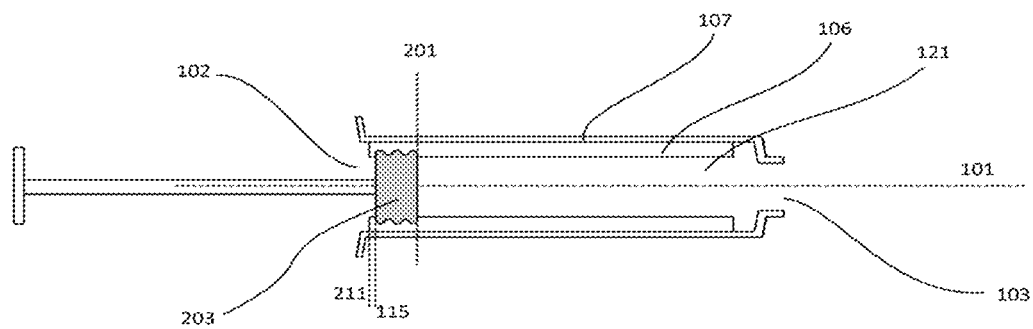

FIG. 4B shows the receptacle 100 of FIG. 4A with a charge 203 located in the interior 121. The front end of the charge 203 is at an axial position 201 along the axis, close to the first aperture 102. The back end of the charge 203 is at p1, close to the start of the lubricant layer 107.

Figure 4C:
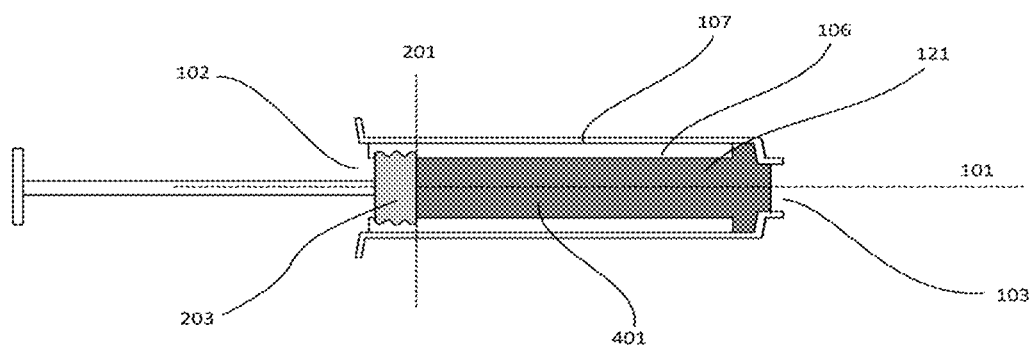

FIG. 4C shows the receptacle 100 of FIG. 4B after having been filled with a liquid pharmaceutical composition 401. The liquid pharmaceutical composition 401 is located in the interior 121 between the front end of the charge 201 and the second aperture 103. In this form, the receptacle 100, the charge 203 and the liquid pharmaceutical composition 401 constitute an assembly.

Figure 4D:
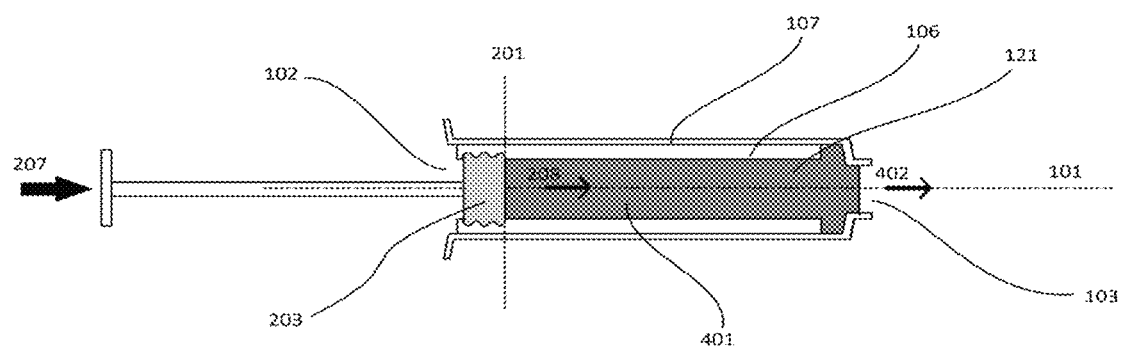

FIG. 4D shows the assembly of FIG. 4C in which a pushing force 207 is applied to push the charge 203 along the axis 101 in a direction from the first aperture 102 towards the second aperture 103. The motion 208 of the charge 203 forces the liquid pharmaceutical composition 401 to be ejected 402 from the receptacle 100.

Figure 4E:
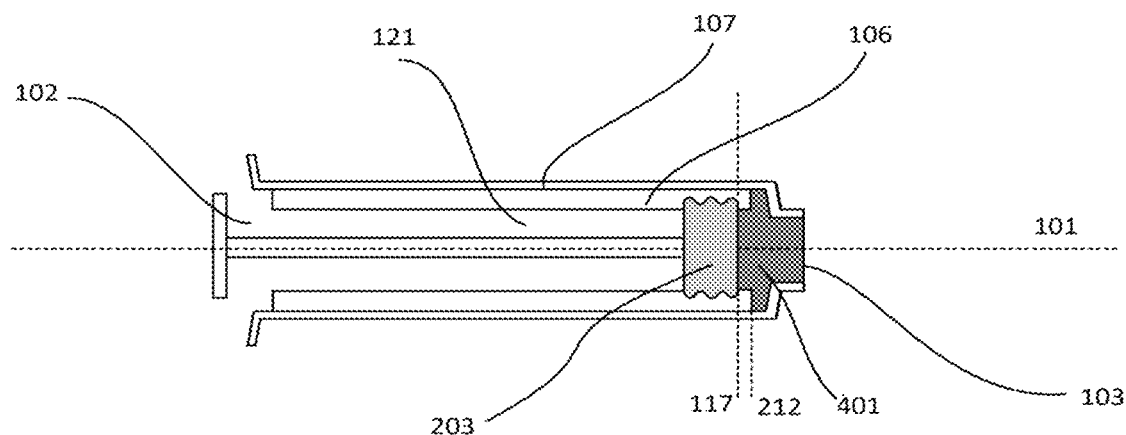

FIG. 4E shows the assembly of FIG. 4D once the charge 203 has travelled along the axis 101 in a direction from the first aperture 102 towards the second aperture 103 to arrive at axial position p2 near the end of the layer 106 of lubricant. The liquid pharmaceutical composition 401 has been ejected via the second aperture 103 and only a small quantity remains in the tip of the receptacle at the second aperture 103.

Figure 5:
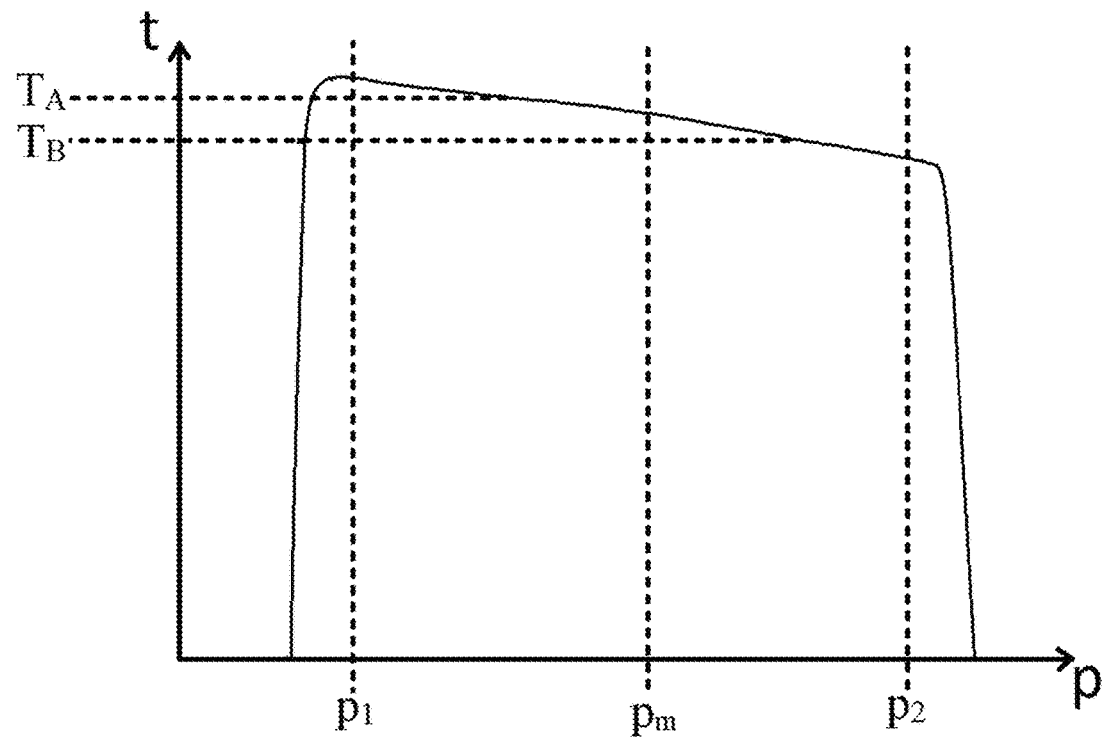
FIG. 5 illustrates a thickness profile of the layer of lubricant.

FIG. 5 shows a thickness profile of the lubricant layer 106 against position partitioned along the position axis. The thickness of the layer 106 drops off rapidly at the endpoints. The portion X from p1 to p2 is thus displaced slightly from the end positions of the layer (106) in order to avoid these end effects. The thickness is well behaved over the portion X. TA is the mean thickness for the section extending from p1 to the midpoint pm. TB is the mean thickness for the section extending from pm to p2. Even were the thickness profile to exhibit local variation over short ranges, the long-range slope of the distribution would be apparent from the means TA and TB. According to the present invention, a relatively flat thickness profile may be advantageous, as expressed by the relevant features disclosed herein. In this case, it can be seen that the thickness profile decreases lightly in a direction from p1 to p2. Possible alternatives are a flat thickness profile without a gradient or a thickness profile which increases lightly in a direction from p1 to p2. A thickness profile having a large gradient, either increasing or decreasing from p1 to p2, is not preferred according to the present invention.

Figure 6:
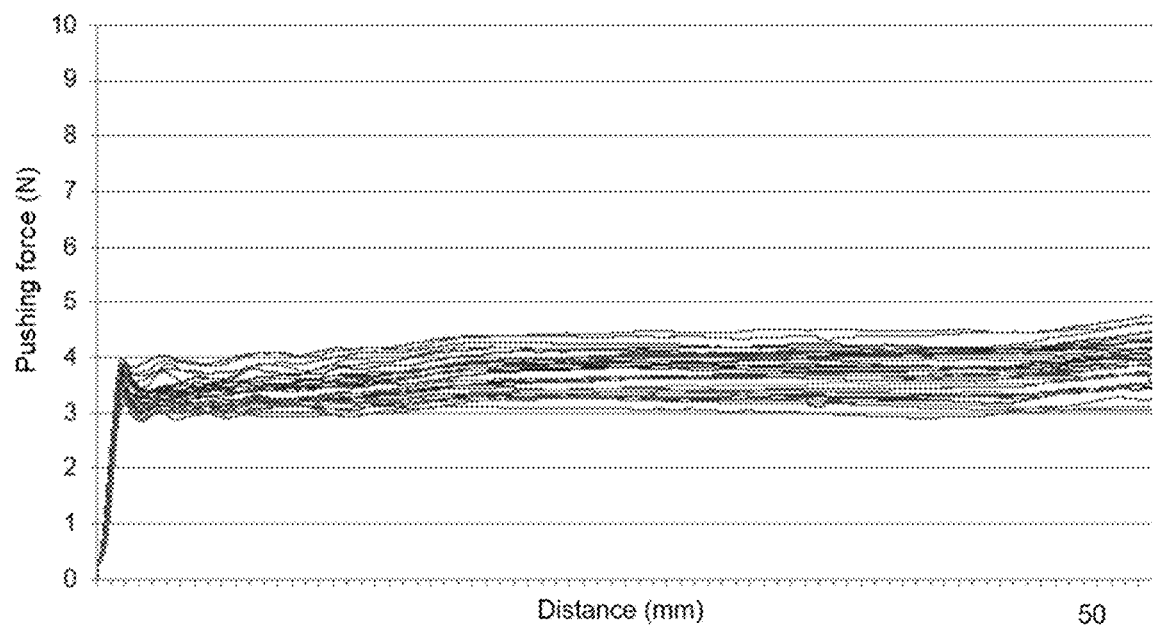
FIG. 6 illustrates a gliding force profile for an exemplary embodiment of a kit provided according to the present invention.

FIG. 6 shows a dynamic friction profile for an exemplary embodiment of a kit provided according to the present invention. The dynamic friction profile is determined using the procedure as presented in the FIGS. 2A to 2G. The test was performed multiple times with fresh kits (all lines shown in the figure). In each run, a smooth level dynamic friction profile was observed with a value in the range from around 3 to 4 N, varying slightly between individual runs. The smooth level dynamic friction profile is well suited to be employed in a single-dose syringe and is particularly favorable for use in automated delivery systems.

Test Methods
Layer Thickness

The thickness of the layer is determined by optical interference measurements using the RapID Explorer available from rap.ID Particle Systems GmbH. Measurements are taken from outside the receptacle through the side wall. The device is operated with the proprietary software and in accordance with the 2014 proprietary instruction manual.

Surface Roughness

Surface roughness of the inner surface of the side wall is measured using a white-light interference microscope. An area of the sample of 2 μm by 2 μm is scanned in tapping mode, scanning the area with 256 lines per picture and 256 dots per line. The scan rate is 0.7 Hz. The cantilever has a tip with a tip radius of ≤10 nm. The sample's topography is measured by evaluating the change of the amplitude of the oscillating cantilever when scanning the surface. The raw data is levelled by a line fit, using a $3^{rd}$ order polynomial fit. The root mean squared roughness Rrms is calculated by the AFM's software using the formula $R_{rms} = \sqrt{1/n \Sigma_{i=1}^{n} y_i^2}$, where n=256*256=65536 and yi is the height value at each of the 65536 measured positions.

Resistive Force

Resistive force is measured using a TesT 106.2 kN device commercially available from TesT GmbH, Germany. The charge is moved with a speed of 100 mm/minute.

EXAMPLES

The following examples are for further elucidation of the present invention and do not limit the scope of the claimed invention.

A lubricant was prepared as follows: 10 g of a vinyl-functionalized polydimethylsiloxane were initially charged in a reaction vessel and admixed with 65 g of decamethyl-cyclopentasiloxane. Under constant stirring at 800 rpm, 0.5 g of methylhydrosiloxane/dimethylsiloxane copolymer, 6.25 g of liquid polydimethylsiloxane, 0.01 g of 10% hexachloroplatinic acid in isopropanol as catalyst and 0.05 g of 2,4,7,9-tetramethyl-5-decyne-4,7-diol as inhibitor were added to this reaction mixture. The reaction solution was used after a stirring time of 60 s. A receptacle was provided according to FIG. 1. The receptacle was a 1 ml 1 g TopPac available from Schott AG Germany. The inner surface of the side walls of the barrel section was coated with the lubricant layer, extending up to 1 mm from each of the two ends of the barrel section. The thickness profile of the applied layer was according to Examples 1-5 of Table 1. The lubricant layer was cured by heating at 175° C. for 20 seconds. The receptacle was tested by introducing a charge made of elastomer with an attached elongate rod according to FIG. 2A, charge FM 257/2 available from Dedecke GmbH, Germany. A process similar to that displayed in FIGS. 2A to 2G, with measurement at 5, 15, 30 and 45 mm along the barrel, was performed to determine the dynamic friction along the barrel of Examples 1-5, as shown in Table 2. The constant velocity of the charge during the measurement movement was 100 mm/min. The process is performed using a TesT 106.2 kN device commercially available from TesT GmbH, Germany.

The root mean square of the roughness of the inner surface of the side wall over the section from p1 to p2 was determined to be 62 nm.

TABLE 1

| Example | Distance along barrel [mm] | | | | | | |
|---|---|---|---|---|---|---|---|
| | 0 | 10 | 20 | 30 | 40 | 50 | 60 |
| | Thickness t [nm] | | | | | | |
| 1 | 704 | 699 | 680 | 713 | 728 | 684 | 705 |
| 2 | 2011 | 2001 | 1988 | 2004 | 1992 | 2014 | 2033 |
| 3 | 708 | 679 | 663 | 665 | 654 | 647 | 641 |
| 4 | 69 | 287 | 714 | 1008 | 1274 | 1678 | 1914 |
| 5 | 2113 | 1711 | 1188 | 1012 | 698 | 301 | 74 |

TABLE 2

| Example | Distance along barrel [mm] | | | |
|---|---|---|---|---|
| | 5 | 15 | 30 | 45 |
| | Dynamic friction [N] | | | |
| 1 | 4.1 | 4.3 | 4.1 | 4.2 |
| 2 | 3.8 | 3.8 | 3.9 | 3.7 |
| 3 | 4.0 | 4.2 | 4.2 | 4.1 |
| 4 | 6.1 | 4.8 | 4.4 | 3.8 |
| 5 | 5.6 | 6.4 | 6.3 | 7.0 |

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE NUMERAL LIST

100 Receptacle
101 Axis
102 First aperture
103 Second aperture
104 Attachment element at front end of receptacle
105 Outwardly protruding flange of receptacle
106 Layer of lubricant
107 Side wall of receptacle
118 Inner surface of side wall
119 First end of receptacle
120 Second end of receptacle
121 Interior of receptacle
201 Initial charge axial position
202 Elongate rod for pushing charge
203 Charge
204 First intermediate charge axial position
205 Second intermediate charge axial position
206 Final charge axial position
207 Pushing force
208 Movement of charge along axis
210 Thickness of layer at a general axial position
301 Thicknesses of the side wall
302 Thicknesses of the layer
401 Liquid pharmaceutical composition
402 Ejection of liquid pharmaceutical composition
501 Elongate barrel section

What is claimed is:

1. A receptacle for pharmaceutical packaging, comprising:
an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB;
a side wall extending over the elongate barrel section, the side wall having an inner surface bordering an interior, the interior having a diameter; and
a layer of a lubricant located on at least a part of the inner surface, at a given axial position p on the axis between pA and pB, a thickness of the side wall, a thickness of the layer, and the diameter of the interior are each determined as an angular mean in a cross-sectional plane perpendicular to the axis at the axial position p, a portion X of the axis extends from a first axial position p1 to a second axial position p2 such that the following criteria are satisfied:
both the first axial position p1 and the second axial position p2 lie between pA and pB;
a portion length LX is a distance between the first axial position p1 and the second axial position p2;
the portion length LX is at least a half of the elongate barrel section length LB; and
the layer extends over the entire portion X; a mean thickness Tmean of the layer is determined in the portion X; a position pm is the midpoint between p1 and p2; TA is a mean thickness of the layer for a section from p1 to pm; TB is a mean thickness of the layer for a section from pm to p2; a ratio TA:TB is in a range from 5:1 to 1:5; wherein the layer has a maximum layer thickness Tmax determined between p1 and p2, a minimum layer thickness Tmin determined between p1 and p2 and a value of Tmin/Tmax is at least 0.7, and one or more criteria are satisfied, the criteria being selected from the group consisting of:
the elongate barrel section length LB is in a range from 3 cm to 20 cm;
a mean value of the diameter of the interior determined over the range pA to pB is in a range from 0.4 cm to 4 cm;
a mean thickness of the sidewall determined over the range pA to pB is in a range from 0.3 mm to 4 mm; and
a volume of the interior is in a range from 0.1 mL to 150 mL.

2. The receptacle of claim 1, wherein the mean thickness Tmean of the layer is in the range from 100 nm to 3000 nm.

3. The receptacle of claim 1, wherein the inner surface of the side wall has a root mean squared surface roughness rrms and a ratio rrms:Tmean is in a range from 1:2 to 1:20.

4. The receptacle of claim 3, wherein the ratio rrms:Tmean is in a range from 1:4 to 1:10.

5. The receptacle of claim 1, wherein the value of Tmin/Tmax is at least 0.9.

6. The receptacle of claim 1, wherein the side wall comprises at least one of a plastic or a glass.

7. The receptacle of claim 1, wherein the lubricant comprises at least one silicone oil.

8. The receptacle of claim 7, wherein the at least one silicone oil is at least partially contained in a matrix.

9. The receptacle of claim 7, wherein the at least one silicone oil comprises at least 25 wt % of a total weight of the lubricant.

10. The receptacle of claim 1, wherein the interior is cylindrical or truncated conical over the elongate barrel section.

11. The receptacle of claim 1, further comprising a first aperture at a first end and a second aperture at a second end.

12. The receptacle of claim 11, wherein the first aperture defines a surface area that is at least 50% greater than a surface area of the second aperture.

13. The receptacle of claim 1, further comprising an attachment element at an aperture.

14. The receptacle of claim 1, wherein the layer defines a mean thickness TA over a first half of the layer and a mean thickness TB over a second half of the layer, a ratio of the mean thicknesses TA:TB being in a range from 1:5 to 5:1.

15. The receptacle of claim 1, wherein the layer has a first thickness t1 at the first axial position p1 and a second thickness t2 at the second axial position, a ratio of the second thickness t2: the first thickness t1 being in a range from 5:1 to 1:5.

16. The receptacle of claim 1, wherein the layer has a minimum thickness tmin between the first axial position p1 and the second axial position p2 that is greater than a mean roughness of the sidewall between the first axial position p1 and the second axial position p2.

17. A kit, comprising:
a receptacle, the receptacle comprising:
an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB;
a side wall extending over the elongate barrel section, the side wall having an inner surface bordering an interior, the interior having a diameter; and
a layer of a lubricant located on at least a part of the inner surface, at a given axial position p on the axis between pA and pB, a thickness of the side wall, a thickness of the layer, and the diameter of the interior are each determined as an angular mean in a cross-sectional plane perpendicular to the axis at the axial position p, a portion X of the axis extends from a first axial position p1 to a second axial position p2 such that the following criteria are satisfied:
both the first axial position p1 and the second axial position p2 lie between pA and pB;
a portion length LX is a distance between the first axial position p1 and the second axial position p2;
the portion length LX is at least a half of the elongate barrel section length LB; and
the layer extends over the entire portion X; a mean thickness Tmean of the layer is determined in the portion X; a position pm is the midpoint between p1 and p2; TA is a mean thickness of the layer for a section from p1 to pm; TB is a mean thickness of the layer for a section from pm to p2; a ratio TA:TB is in a range from 5:1 to 1:5; wherein the layer has a maximum layer thickness Tmax determined between p1 and p2, a minimum layer thickness Tmin determined between p1 and p2 and a value of Tmin/Tmax is at least 0.7, and one or more criteria are satisfied, the criteria being selected from the group consisting of:

the elongate barrel section length LB is in a range from 3 cm to 20 cm;
a mean value of the diameter of the interior determined over the range pA to pB is in a range from 0.4 cm to 4 cm;
a mean thickness of the sidewall determined over the range pA to pB is in a range from 0.3 mm to 4 mm; and
a volume of the interior is in a range from 0.1 mL to 150 mL; and a charge adapted and arranged to be positioned in the interior such that:
the charge seals a cross section of the interior between inner surfaces of the side walls;
the charge has a front end at the axial position closest to pB at which the charge contacts the layer or the inner surface;
the charge has a back end at the axial position closest to pA at which the charge contacts the layer or the inner surface;
a length of the charge LC is a distance between the front end and the back end;
the charge has a charge axial position that is an axial position of the front end; and
the charge is movable in a direction parallel to the axis with a dynamic friction g that is a function of the charge axial position.

18. The kit of claim 17, wherein for charge axial positions in a range from the first axial position p1+the length of the charge LC to the second axial position p2, the dynamic friction g has a standard deviation gSD less than 2 N.

19. An assembly, comprising:
a receptacle, the receptacle comprising:
an elongate barrel section having a direction of elongate extension and an axis in the direction of elongate extension, an axial position p being determined along the axis, the elongate barrel section extending from an axial position pA to an axial position pB, an elongate barrel section length LB being a distance between pA and pB;
a side wall extending over the elongate barrel section, the side wall having an inner surface bordering an interior, the interior having a diameter;
an aperture; and
a layer of a lubricant located on at least a part of the inner surface, at a given axial position p on the axis between pA and pB, a thickness of the side wall, a thickness of the layer, and the diameter of the interior are each determined as an angular mean in a cross-sectional plane perpendicular to the axis at the axial position p, a portion X of the axis extends from a first axial position p1 to a second axial position p2 such that the following criteria are satisfied:
both the first axial position p1 and the second axial position p2 lie between pA and pB;
a portion length LX is a distance between the first axial position p1 and the second axial position p2;
the portion length LX is at least a half of the elongate barrel section length LB; and
the layer extends over the entire portion X; a mean thickness Tmean of the layer is determined in the portion X; a position pm is the midpoint between p1 and p2; TA is a mean thickness of the layer for a section from p1 to pm; TB is a mean thickness of the layer for a section from pm to p2; a ratio TA:TB is in a range from 5:1 to 1:5; wherein the layer has a maximum layer thickness Tmax determined between p1 and p2, a minimum layer thickness Tmin determined between p1 and p2 and a value of Tmin/Tmax is at least 0.7, and one or more criteria are satisfied, the criteria being selected from the group consisting of:
- the elongate barrel section length LB is in a range from 3 cm to 20 cm;
- a mean value of the diameter of the interior determined over the range pA to pB is in a range from 0.4 cm to 4 cm;
- a mean thickness of the sidewall determined over the range pA to pB is in a range from 0.3 mm to 4 mm; and
- a volume of the interior is in a range from 0.1 mL to 150 mL;

a charge positioned in the interior sealing a cross section of the interior; and a liquid pharmaceutical composition contained in the interior and located between the sealed cross section and the aperture, the assembly being adapted and arranged for the liquid pharmaceutical composition to be ejected through the aperture by movement of the charge in a direction parallel to the axis.

\* \* \* \* \*